US012161584B2

(12) United States Patent
Decock (10) Patent No.: US 12,161,584 B2
(45) Date of Patent: Dec. 10, 2024

(54) METHOD FOR MONITORING THE DISPENSING OF A DROP AND ASSISTANCE DEVICE

(71) Applicant: Nemera La Verpillière, La Verpilliere (FR)

(72) Inventor: Thierry Decock, Lyons (FR)

(73) Assignee: NEMERA LA VERPILLIÈRE, La Verpillière (FR)

( * ) Notice: Subject to any disclaimer, the term of this patent is extended or adjusted under 35 U.S.C. 154(b) by 1041 days.

(21) Appl. No.: 16/967,996

(22) PCT Filed: Feb. 5, 2019

(86) PCT No.: PCT/EP2019/052767
§ 371 (c)(1),
(2) Date: Dec. 24, 2020

(87) PCT Pub. No.: WO2019/154803
PCT Pub. Date: Aug. 15, 2019

(65) Prior Publication Data
US 2021/0113371 A1    Apr. 22, 2021

(30) Foreign Application Priority Data
Feb. 6, 2018    (FR) ...................................... 1850986

(51) Int. Cl.
*A61F 9/00*    (2006.01)
*A61M 5/14*    (2006.01)
(Continued)

(52) U.S. Cl.
CPC ............. *A61F 9/0008* (2013.01); *A61M 5/14* (2013.01); *A61M 5/168* (2013.01);
(Continued)

(58) Field of Classification Search
CPC ...... A61F 9/0008; A61F 9/0026; G01F 22/00; G01L 1/22; A61M 5/1689; A61M 5/14;
(Continued)

(56) References Cited

U.S. PATENT DOCUMENTS 4,038,981 A * 8/1977 LeFevre ............... A61M 5/1411
128/DIG. 13
4,094,318 A * 6/1978 Burke .................. A61M 5/1689
604/245
(Continued)

FOREIGN PATENT DOCUMENTS

| CN | 105163777 A | 12/2015 | |
|---|---|---|---|
| CN | 115300172 A * | 11/2022 | ............. A61B 5/022 |

(Continued)

*Primary Examiner* — Susan S Su
*Assistant Examiner* — Ted Yang
(74) *Attorney, Agent, or Firm* — Farber LLC; Jonathan Winter (57) ABSTRACT

A method for monitoring the dispensing of a drop by a device for dispensing a liquid product in the form of drops uses a detector for detecting a liquid product arranged near an orifice for dispensing drops, and a system for processing information provided by the detector. The processing system receives information corresponding to the series of steps: detecting the presence of liquid, wherein the detector detects the presence of liquid near the dispensing orifice, the detector configured such that detection of the presence of liquid is indicative of a drop in the course of being formed, in contact with the dispensing orifice, and detecting an absence of liquid, wherein the detector detects the absence of liquid near the dispensing orifice, and the processing system processes the series of information on detection of the presence and absence of liquid in order to provide information on the dispensing of a drop.

20 Claims, 2 Drawing Sheets

(51) Int. Cl.
*A61M 5/168* (2006.01)
*G01F 22/00* (2006.01)
*G01L 1/22* (2006.01)
*G01P 13/00* (2006.01)

(52) U.S. Cl.
CPC .... *A61M 5/16804* (2013.01); *A61M 5/16831* (2013.01); *A61M 5/16886* (2013.01); *A61M 5/1689* (2013.01); *G01F 22/00* (2013.01); *G01L 1/22* (2013.01); *G01P 13/0066* (2013.01)

(58) Field of Classification Search
CPC .............. A61M 5/168; A61M 5/16804; A61M 5/16831; A61M 5/16886; G01P 13/0066
See application file for complete search history.

(56) References Cited

U.S. PATENT DOCUMENTS

| | | | |
|---|---|---|---|
| 4,105,028 A | 8/1978 | Sadlier et al. | |
| 4,321,461 A * | 3/1982 | Walter, Jr. | A61M 5/1689 377/53 |
| 4,328,800 A * | 5/1982 | Marx | A61M 5/1689 604/122 |
| 4,328,801 A * | 5/1982 | Marx | A61M 5/1689 604/67 |
| 4,623,331 A * | 11/1986 | Cewers | A61M 5/1689 604/65 |
| 4,635,281 A * | 1/1987 | Jones | A61M 5/1689 377/21 |
| 4,680,462 A * | 7/1987 | Kamen | A61M 5/1689 250/222.1 |
| 4,681,569 A * | 7/1987 | Coble | A61M 5/1689 73/861.41 |
| 4,820,281 A * | 4/1989 | Lawler, Jr. | A61M 5/1689 D24/129 |
| 4,821,028 A * | 4/1989 | Deckert | A61M 5/1689 128/DIG. 13 |
| 5,002,539 A * | 3/1991 | Coble | A61M 5/1689 73/861.41 |
| 5,012,496 A * | 4/1991 | Weinreb | A61F 9/0008 377/6 |
| 5,152,424 A * | 10/1992 | Weinreb | A61F 9/0008 222/14 |
| 5,186,057 A * | 2/1993 | Everhart | G01B 11/00 356/627 |
| 5,207,659 A * | 5/1993 | Pennaneac'h | B05B 11/1015 417/489 |
| 5,938,643 A * | 8/1999 | Lerner | A61M 5/1689 604/251 |
| 8,998,861 B2 * | 4/2015 | Fateh | A61F 9/0017 604/289 |
| 10,152,867 B2 * | 12/2018 | Fateh | A61F 9/0026 |
| 10,537,468 B2 * | 1/2020 | Fateh | A61F 9/0026 |
| 2004/0039355 A1 * | 2/2004 | Gonzalez | A61M 11/00 604/298 |
| 2004/0167499 A1 | 8/2004 | Grove et al. | |
| 2004/0254527 A1 * | 12/2004 | Vitello | B41J 2/17513 604/82 |
| 2006/0031099 A1 * | 2/2006 | Vitello | G16H 20/17 604/82 |
| 2007/0241286 A1 * | 10/2007 | Greenwald | A61M 1/3626 604/122 |
| 2009/0153148 A1 * | 6/2009 | Greenwald | A61M 1/3626 324/639 |
| 2009/0227939 A1 * | 9/2009 | Mernoe | A61M 39/286 356/442 |
| 2010/0286634 A1 * | 11/2010 | Marx | A61F 9/0026 340/815.4 |
| 2012/0143152 A1 * | 6/2012 | Hunter | B05B 17/0676 604/290 |
| 2013/0336814 A1 * | 12/2013 | Kamen | A61M 5/1689 417/302 |
| 2014/0228783 A1 * | 8/2014 | Kraft | G07F 15/04 604/300 |
| 2014/0257206 A1 * | 9/2014 | Fateh | A61F 9/0017 604/290 |
| 2014/0276476 A1 * | 9/2014 | Fateh | A61F 9/0017 604/290 |
| 2015/0018781 A1 * | 1/2015 | Rinderknect | A61F 9/0026 604/298 |
| 2015/0173945 A1 * | 6/2015 | Fateh | A61F 9/0026 604/300 |
| 2015/0289805 A1 * | 10/2015 | Eaton | G16H 20/13 604/290 |
| 2016/0220180 A1 * | 8/2016 | Fateh | A61J 7/0427 |
| 2016/0239635 A1 * | 8/2016 | Fateh | A61M 15/008 |
| 2017/0216521 A1 * | 8/2017 | Kolko | G01F 3/00 |
| 2020/0113733 A1 * | 4/2020 | Fateh | A61F 9/0026 |
| 2020/0338263 A1 * | 10/2020 | Wollowitz | A61M 39/28 |
| 2020/0360180 A1 * | 11/2020 | Stowe | A61F 9/0026 |
| 2020/0363313 A1 * | 11/2020 | Azar | G01N 15/1434 |

FOREIGN PATENT DOCUMENTS

| | | | |
|---|---|---|---|
| DE | 202016003139 U1 | 6/2016 | |
| EP | 1656923 A1 * | 5/2006 | .............. A61J 7/04 |
| WO | 2009148345 A2 | 12/2009 | |
| WO | 2014066546 A1 | 5/2014 | |
| WO | 2014130974 A1 | 8/2014 | |
| WO | WO-2016183394 A1 * | 11/2016 | ........... A61F 9/0008 |

* cited by examiner

METHOD FOR MONITORING THE DISPENSING OF A DROP AND ASSISTANCE DEVICE

FIELD OF THE INVENTION

The invention relates to a method for monitoring the dispensing of a drop by a device for dispensing a liquid product in the form of drops and to an assistance device for assisting in the use of such a dispensing device.

BACKGROUND OF THE INVENTION

When dispensing a liquid product in the form of drops, it may be interesting to know whether the drop has been dispensed. For example for the administration of medical products, it is interesting, both for the user and for monitoring the dose, to detect the dispensing of a drop to control the amount of medication administered. For example, an underdose or overdose of medication must be avoided to preserve the patient's health, and also, knowing the amount of product dispensed, the amount of product remaining in the dispensing device can be calculated.

US 2014/0257206 describes a device for controlling the instillation of drops of ophthalmic liquid comprising an optical drop detector capable of detecting the passage of a drop. However, this method cannot detect that a drop has actually been dispensed into the eye of the subject.

The invention aims in particular to provide a method for monitoring the dispensing of a drop and an assistance device to determine more easily whether a drop has actually been dispensed.

SUMMARY OF THE INVENTION

The invention therefore relates in particular to a method for monitoring the dispensing of a drop by a device for dispensing a liquid product in the form of drops, using means for detecting a liquid product which are arranged near an orifice for dispensing drops, and a system for processing information provided by the detection means, a monitoring method during which the processing system receives information corresponding to the following series of steps:
- a step of detecting the presence of liquid, during which the detection means detect the presence of liquid near the dispensing orifice, the detection means being configured such that the detection of the presence of liquid is indicative of a drop in the course of being formed, in contact with the dispensing orifice,
- a step of detecting an absence of liquid, during which the detection means detect the absence of liquid near the dispensing orifice, and the processing system processes the series of information on detection of the presence and absence of liquid in order to provide information on the dispensing of a drop.

The monitoring method thus provides information relating to the disappearance of a drop near the dispensing orifice, by observing a presence and then an absence of a drop, at the same position and during two successive steps. Thus, the sequence of "presence, absence" of a drop can be used to determine whether the drop formed has fallen. In particular, it can be used to take into account the cases of incorrect use of the dispensing device, which could not necessarily be detected by simply observing the appearance of a drop, without then observing whether the drop is absent, in particular because it has detached from the dispensing orifice. For example, when the pressure applied on the dispensing device is too low, the detected drop may not be dispensed and may remain in place as a residual drop. The proposed monitoring method can therefore be used to detect this residual drop and thus deduce that the drop has not detached, in order, for example, to inform the user accordingly and/or to avoid having an incorrect count of drops dispensed or to be dispensed.

The information provided by the processing system after the monitoring method is, for example, information used to assign a correct dispensing of a drop, when the sequence of "presence, absence" has actually been detected, and/or information used to assign an incorrect dispensing of a drop, when this sequence is not detected.

Note that the information processing may take into account other information made available to the processing system, for example, to complete or improve the information provided. This information is for example the pressure exerted on the dispensing device, the duration of the presence of the drop detected near the dispensing orifice, etc.

It is understood that the detection means are configured, not only so that the detection of the presence of liquid near the dispensing orifice is indicative of a drop in the course of being formed, in contact with the dispensing orifice, but also so that the detection of absence of liquid near said dispensing orifice is indicative of a drop which has detached from the dispensing orifice, and which is therefore no longer in contact with the dispensing orifice. A "drop in the course of being formed" means a drop of liquid that has not detached from the dispensing orifice. Thus, liquid in contact with the dispensing orifice, for a short or a long period of time, and which has therefore not detached thereof, is considered to be a "drop being formed".

The monitoring method may further comprise one or more of the following characteristics, taken alone or in combination.

The monitoring method comprises, before the step of detecting the presence of liquid, referred to as the second detection step, a step of detecting the absence of liquid, referred to as the first detection step, during which the detection means detect the absence of liquid near the dispensing orifice. This first detection step is particularly advantageous since it can be used to identify not only a drop that has detached from the dispensing orifice, but also the appearance of a drop near the dispensing orifice, by observing an absence and then a presence of a drop. Thus, the sequence of "absence, presence, absence" of a drop can be used to determine whether the drop has just been formed and has fallen. In particular, it is then possible to check that the dispensing orifice does not contain a residual drop, which may present a risk of contamination if it is has been residual for a certain period of time, or which may imply an unsuitable drop size. In a particularly advantageous manner, when this first detection step does not occur, the assistance device can be designed to indicate a malfunction so that the user is prompted to clean the dispensing orifice in order to remove the residual drop.

The monitoring method comprises, before the step of detecting the presence of liquid, referred to as the second detection step, a step of detecting activation of the dispensing of a drop, for example following a pressure exerted on a bearing area or a certain inclination of the dispensing device. This previous step of detecting an activation is advantageous since it can be used to ensure that the liquid detected during the second detection step is due to a deliberate activation of the dispensing of a drop. For example, if a drop is dispensed into a first eye and then another into the second eye, it may not be possible to detect an absence of liquid during a first detection step, due to residual liquid in the dispensing orifice between dispensing into the first eye and dispensing into the second eye. Nevertheless, this residual liquid is not a problem since it is not exposed to the air for a long period of time, and therefore not likely to be contaminated. According to another advantage of this previous step of detecting an activation, it would be possible to only activate the detection means at a time when the user starts to use the assistance device and therefore starts to activate the dispensing of a drop. This saves energy, as in this case there is not necessarily sufficient time, before detecting the presence of liquid, to detect an absence of liquid.

The detection means transmit a detection signal near the dispensing orifice, receive said transmitted detection signal and detect the presence of liquid by receiving a detection signal that is disturbed compared with a detection signal received in the absence of liquid, the detection signal preferably being an optical signal, for example an infrared ray. "Optical" means any electromagnetic wave, belonging to the visible or non-visible spectrum. The optical detection means used for this purpose are generally means capable of transmitting, receiving and/or reflecting such a wave. The optical detection means comprise a transmitter and a receiver, either separate and preferably diametrically opposed relative to the dispensing orifice, or combined or adjacent on the same component and receiving a detection signal by a possible reflection on an opposite wall.

The monitoring method comprises a step during which the time elapsed between the start of the step of detecting the presence of liquid and the start of the step of detecting the absence of liquid is measured and the processing system assigns an incorrect dispensing of a drop when the time elapsed is less than a first predetermined duration threshold and preferably the information corresponding to this incorrect or correct dispensing is provided to a user. The viscosity of the liquid product and the drop formation duration affect the volume of the drop. In particular, the volume of the drop deviates from an ideal or theoretical volume when the formation duration is too short, for example due to a very high pressure exerted suddenly on the tank. Thus, when the drop formation duration is less than the first predetermined duration threshold, for example 1 second, the processing system considers that the amount of liquid product dispensed is quite different from the optimum amount of liquid product to be dispensed and the dispensing is incorrect. Alternatively, the processing system can be configured so that it assigns a correct dispensing as long as liquid product is being dispensed, regardless of the volume of the dispensed drop. In this case, the processing system can assign a correct dispensing although the drop size is not optimum. It is understood that the drop formation duration is the time which has elapsed between the moment when no start of drop formation is initiated and the moment when the drop has detached. Since these two moments are difficult to detect, it is chosen to measure the time elapsed between the moment when a start of drop formation is detected, i.e. the start of the step of detecting the presence of liquid, and the moment when the detachment of the drop is detected by its absence following its presence near the dispensing orifice, i.e. the end of the step of detecting the presence of liquid coinciding with the start of the step of detecting the absence of liquid. This applies throughout the description to any characteristic referring to the drop formation duration. Since the drop formation duration depends on the viscosity of the liquid product, the first predetermined duration threshold is predefined according to the viscosity of the liquid product used.

The monitoring method comprises a step during which the time elapsed between the start of the step of detecting the presence of liquid and the start of the step of detecting the absence of liquid is measured and the processing system assigns an incorrect dispensing of a drop when the time elapsed is greater than a second predetermined duration threshold. Preferably, information corresponding to this incorrect dispensing is made available to a user. It is advantageous that the processing system should consider that the dispensing of a drop is correct when the drop formation duration is less than the second predetermined duration threshold. In fact, if the drop takes too long to fall, i.e. the drop formation duration is greater than the second predetermined duration threshold, it may be assumed that the drop is not dispensed into the receiving organ and that it is a residual drop removed afterwards, for example because the assistance device is not kept inclined for long enough and/or the pressure exerted on the dispensing device to dispense the drop is too low. In this situation, the dispensing of the drop can be considered to be invalid. By advantageously making this information available to the user, the latter can then be prompted to dispense another drop to make up for the missing drop.

The two previous embodiments can be combined. Thus, it is particularly advantageous that the processing system should consider that the dispensing of a drop is correct when the drop formation duration is between the first and second predetermined duration thresholds. If the drop formation duration is greater than the first predetermined duration threshold, the processing system may consider that the volume of the detected drop is optimum, substantially equal to an ideal or theoretical volume, as explained previously. Furthermore, if the drop formation duration is less than the second predetermined duration threshold, the processing system may consider that the drop has been dispensed into the eye. Thus, by making these comparisons with either or both of the first and second predetermined duration thresholds, the monitoring method can be used not only to detect that a drop has fallen, with the sequence "presence, absence", but also to monitor that the drop has fallen with an optimum size and at the right time, therefore at the right place. This embodiment in which comparisons are made with the first predetermined duration threshold and/or the second predetermined duration threshold is therefore particularly relevant.

The monitoring method comprises the following steps:
  determining a theoretical drop volume, preferably based on the geometric characteristics of the dispensing orifice and the viscosity of the liquid product, and preferably also on other characteristics of the dispensing device,
  measuring the time elapsed between the start of the step of detecting the presence of liquid and the start of the step of detecting the absence of liquid,
  using this elapsed time to weight the theoretical drop volume and estimate a volume of the dispensed drop.

In particular, the theoretical volume is weighted if the time measured is less than a first predetermined duration threshold.

Thus, the time elapsed can be used to estimate the volume of the drop dispensed, and therefore the remaining dose. We see in particular that for liquid products of relatively low viscosity, for example less than 100 cP, the volume of the dispensed drop can be smaller when the drop formation duration is shorter. Furthermore, for liquid products of higher viscosity, for example greater than 100 cP, the volume of the dispensed drop can be greater when the drop formation duration is shorter. Thus, to accurately determine the volume of the dispensed drop, the theoretical drop volume can be weighted with the measured duration to obtain an estimated volume closer to the actual drop volume dispensed. Other characteristics of the dispensing device which can be taken into account when determining the theoretical volume can be selected from: the resistance of the tank to the pressure exerted by the user, the flow rate limitation exerted by geometric shapes upstream from the dispensing orifice, the characteristics of a dispensing valve or other elements that can affect the link between the pressure exerted by a user on the tank and the drop of liquid product formed.

The monitoring method comprises a step during which the pressure exerted on a bearing area to activate dispensing of a drop is monitored and the means for detecting liquid product are activated when the pressure exceeds a predetermined pressure threshold. The predetermined pressure threshold corresponds, for example, to the minimum pressure to be exerted on the dispensing device to cause the formation of a drop. By keeping the detection means inactive when the pressure is less than the predetermined pressure threshold, their energy consumption is decreased without the risk of not detecting a drop. The pressure is monitored for example by means of a force-sensing resistor, which can be placed for example directly on a bearing area of the assistance device or on a bearing area of the dispensing device, or on an area intended to be connected to the tank of the dispensing device and receiving a certain pressure when activating the dispensing of a drop, or in any other area to which a force is applied when the user exerts a pressure to activate the dispensing of a drop. The threshold is for example 5 N or 15 N. A "bearing area" means an area on which a user presses directly or by means of another element to exert an activation pressure on the tank in order to activate the dispensing of a drop of liquid. The bearing area can be arranged on the assistance device or on the dispensing device.

The monitoring method comprises a step during which the pressure exerted on a bearing area to activate the dispensing of a drop is monitored and the processing system assigns an incorrect dispensing of a drop when the pressure is less than a predetermined pressure threshold, preferably when the lower pressure is exerted for a duration greater than a predetermined duration. Preferably, the processing system assigns an incorrect dispensing of a drop when the pressure is less than the predetermined pressure threshold at the start of the third detection step. In the case of a dispensing device without drop suck-back (dispensing device which, after releasing the pressure, does not suck back a partially formed drop), a drop can be formed by exerting a series of relatively low pressures, for example by repeating pressures corresponding to the minimum pressure to be exerted on the dispensing device to cause the formation of a drop. The dispensing of a drop can then be considered to be correct when this minimum pressure is exerted at the start of the third detection step. When the user applies a pressure (i.e. a force) on the bearing area, this pressure can therefore be expected to exceed the predetermined pressure threshold, and preferably for a sufficient duration, in order to form and especially detach a drop. When the pressure applied is low, the sequence "absence, presence, absence" detected may correspond with a certain probability to an incorrect dispensing, corresponding for example to a partially formed drop that detaches from the orifice due to unwanted shaking for a dispensing device without drop suck-back, or to a partially formed drop which is sucked back inside the dispensing orifice for a dispensing device with suck-back. In both cases, the drop formed will not be dispensed into the receiving organ, hence the fact that the processing system considers that dispensing is incorrect, and it is interesting to be able to initiate an action such as warning the user of an incorrect dispensing. We understand that in the case of dispensing devices without suck-back, the pressure exerted on a bearing area required to assign the correct dispensing of a drop can be exerted in several steps, for example, a first pressure less than the predetermined pressure threshold, then a second pressure less than the predetermined pressure threshold, but the sum of these two pressures being greater than the predetermined pressure threshold if each of the first and second pressures less than the predetermined pressure threshold is nevertheless greater than a predetermined minimum pressure threshold. In this case, the processing system may assign the correct dispensing of a drop, preferably if the two first and second pressures less than the predetermined pressure threshold are separated by a duration less than a predetermined duration.

The monitoring method comprises a step during which the displacement of a bearing area, preferably the duration of this displacement, is monitored, for example using a first accelerometer connected to the bearing area and a second accelerometer connected to the tank of the dispensing device containing the liquid product, and the processing system assigns an incorrect dispensing of a drop when the displacement is less than a predetermined displacement threshold during the second detection step or the duration of the displacement is less than a predetermined duration threshold. Since the displacement of the bearing area reflects the pressure exerted, by measuring this displacement, the pressure exerted on the bearing area is measured indirectly by taking into account its mechanical resistance. Thus, by evaluating the displacement of the bearing area, and preferably also the duration of this displacement, the processing system can determine whether a drop has been formed and dispensed. Furthermore, as for the pressure measurement, the displacement of the bearing area can also be carried out in several steps. In this case, the processing system considers the sum of these displacements, and preferably the sum of the durations of these displacements, and preferably whether these displacements are separated by a duration less than a predetermined duration.

During the step of detecting the absence of liquid, the absence of liquid is detected at a first distance from the dispensing orifice and during a step of detecting the presence of liquid, performed at the same time as, or after, the step of detecting the absence of liquid, the presence of liquid is detected at a second distance from the dispensing orifice, the second distance being greater than the first distance. Said step of detecting the presence of liquid is referred to as the fourth detection step. The distance is defined in the direction from the dispensing orifice to the target organ of a user. An absence of liquid is therefore detected at a distance closer to the dispensing orifice than a presence of liquid. Thus, the detection of an absence of liquid indicates that the drop has left the dispensing orifice and the detection of a presence of liquid slightly further away from the dispensing orifice indicates that the drop has been dispensed out of the orifice. Thus, the processing system detects the dispensing of a drop out of the dispensing device and, for example, discards cases where the drop is sucked back inside the dispensing orifice. The step of detecting the presence of liquid, referred to as the fourth detection step, is performed at the same time as the step of detecting the absence of liquid when the distance between the first and second distances is less than the drop size. The step of detecting the presence of liquid, referred to as the fourth detection step, is performed after the step of detecting the absence of liquid when the distance between the first and second distances is greater than the drop size.

The monitoring method comprises a step during which the inclination of the dispensing device is measured, and the processing system assigns an incorrect dispensing of a drop when the inclination variation exceeds a predetermined value during the second detection step. When the inclination of the dispensing device undergoes a significant change during the formation of the drop, the drop has probably not been dispensed into the receiving organ. This is the case, for example, when the user makes a sudden movement of the dispensing device towards its vertical rest position during the formation of the drop. Advantageously, by combining the measurement of the inclination of the dispensing device and the measurement of the pressure exerted on a bearing area described previously, the processing system can perform a double check of the dispensing of a drop. This can be used, for example, to discard the case where the user exerts a high pressure on the dispensing device when the latter is in its vertical rest position or the case where the user holds the dispensing device in the inclined position without exerting any pressure on the dispensing device. In both cases, there is no correct dispensing of a drop. It is understood that both the acceleration of the dispensing device and the inclination of the dispensing device could be measured, in order to take into account sudden movements with no variation of the inclination.

The monitoring method comprises a step during which the inclination of the dispensing device is measured and the processing system uses this measurement to estimate the volume of the drop detected. Note that the inclination of the dispensing device affects the volume of the drop. More precisely, we see that the volume of the dispensed drop increases with the angle of inclination of the dispensing device measured from the horizontal. Thus, by measuring this inclination, the processing system can weight a theoretical drop volume to estimate the volume of the drop actually dispensed. Furthermore, after obtaining the volume of the drop detected, the processing system can possibly calculate a new value of the residual volume of liquid product in the dispensing device.

The monitoring method comprises:
- a step of determining the theoretical drop volume, preferably based on the geometric characteristics of the dispensing orifice and the viscosity of the liquid product, and preferably also on other characteristics of the dispensing device,
- a step of estimating the volume of the dispensed drop comprising a step of1 weighting the theoretical drop volume, during which at least one of the following parameters is taken into account to perform this weighting:
    - the magnitude of the activation pressure applied by the user on the tank to cause the formation of the drop,
    - the variation profile of this activation pressure over time,
    - the inclination of the assistance device and of the dispensing device,
    - the time during which a signal provided by the detection means is disturbed,
    - the measurement of the weight of the dispensing device.

The theoretical volume preferably corresponds to a volume calculated using fixed data on the liquid product or the dispensing device, which do not vary depending on the conditions of use of the dispensing device. The fixed data can be determined by the information processing system, for example by reading the information shown on the dispensing device, or by manual configuration. By taking into account at least one of the above parameters, the calculated theoretical volume is adjusted to the conditions of use of the dispensing device, in order to obtain a more realistic estimation and therefore a more precise and reliable determination of the amount of liquid product dispensed.

The monitoring method comprises a step during which a contact between a bearing surface of an assistance device for assisting in the use of the dispensing device and the skin of the subject is detected and during which the processing system processes this information to assign a correct dispensing of a drop, preferably when the contact detection occurs at the same time as the start of the step of detecting the absence of liquid. The contact detection indicates that the receiving organ is correctly positioned opposite the dispensing orifice. This guarantees that the drop is dispensed at the right place. In this way, any dispensing of a drop could be prevented if no contact is detected, or information could be sent to the user, or even the processing system could assign an incorrect dispensing of a drop.

The monitoring method comprises a step during which the user is informed when the processing system does not receive the information corresponding to the series of the two steps of detecting the presence of liquid and the absence of liquid, or even when the processing system does not receive the information corresponding to the series of the three steps of detecting the absence of liquid, the presence of liquid and the absence of liquid, or even when the processing system assigns an incorrect dispensing of a drop, for example by a visual, audible or tactile signal. By informing the user of the incorrect dispensing of a drop, the user can, for example, dispense another drop to correct the previous incorrect dispensing. The visual signal can be transmitted by a LED or an alphanumeric display. The tactile signal may consist of vibrations. Alternatively or in combination, the user can be informed when the processing system receives the information corresponding to the series of the two or three detection steps, or when the processing system assigns a correct dispensing of a drop.

The method comprises a step during which the weight of the dispensing device is measured to deduce the amount of liquid product remaining in the dispensing device. Knowing the value of the residual volume obtained by measuring the weight, the amount of liquid product dispensed can be deduced. Thus, the weight measurement can also be used to validate the estimated volume of the drop detected or even to convert the remaining amount of liquid into a theoretical number of remaining drops. The step of measuring the weight can be triggered conditionally depending on the inclination detected, in particular depending on a predetermined period of time during which the dispensing device is kept inclined.

For the cases described previously in which it is planned to measure the time elapsed between the start of the step of detecting the presence of liquid and the start of the step of detecting the absence of liquid, it is also possible as an alternative to measure the time elapsed in a time interval comprising another part of the step of detecting the presence of liquid and/or another part of the step of detecting the absence of liquid.

The invention further relates to an assistance device for assisting in the use of a device for dispensing a liquid product in the form of drops for implementing the above monitoring method, comprising the means for detecting liquid product, the processing system and at least one of the elements from the group comprising:

- means for measuring the time elapsed between the start of the step of detecting the presence of liquid and the start of the step of detecting the absence of liquid,
- means for measuring inclination,
- means for detecting pressure on a bearing area,
- means for detecting contact with the skin of a user,
- means for measuring weight,
- means for indicating information to a user.

Each of these means can be used to provide additional information to the processing system to obtain information on the dispensing of a drop, such as assigning a correct or incorrect dispensing or quantifying the amount of dispensed or remaining liquid product.

The invention also relates to an assistance device for assisting in the use of a device for dispensing a liquid product in the form of drops, comprising

- means for detecting liquid product which are arranged near a drop dispensing orifice, and
- a system for processing the information provided by the detection means, the processing system being configured to provide information on the dispensing of a drop, the means for detecting liquid product comprising first detection means configured to detect liquid at a first distance from the dispensing orifice, and second detection means configured to detect liquid product at a second distance from the dispensing orifice, the second distance being greater than the first distance.

The first and second distances are defined in the direction from the dispensing orifice to the user's receiving organ. Using this assistance device, the detection means can be used to detect the presence or absence of liquid, and therefore a drop, at two different distances from the dispensing orifice. Depending on the result obtained by either the first or second detection means, preferably obtained simultaneously by the two first and second detection means, the processing system can deduce whether a drop of liquid product has only been formed, dispensed, become residual or sucked back inside the orifice. For example, if the first detection means detect the absence of liquid while the second detection means detect the presence of liquid, since the second detection means are further away from the dispensing orifice than the first detection means, the processing system can deduce that a drop of liquid product has detached from the dispensing orifice.

The assistance device may further comprise means for blowing the residual drop, using for example an air nozzle. Thus, if a residual drop is detected, an air flow can be directed towards the dispensing orifice in order to blow the residual drop away from the end of the dispensing orifice.

BRIEF DESCRIPTION OF THE DRAWINGS

We will now describe particular embodiments of the invention given as non-limiting examples referring to the attached figures, on which.

DETAILED DESCRIPTION OF THE INVENTION

Figure 1A:
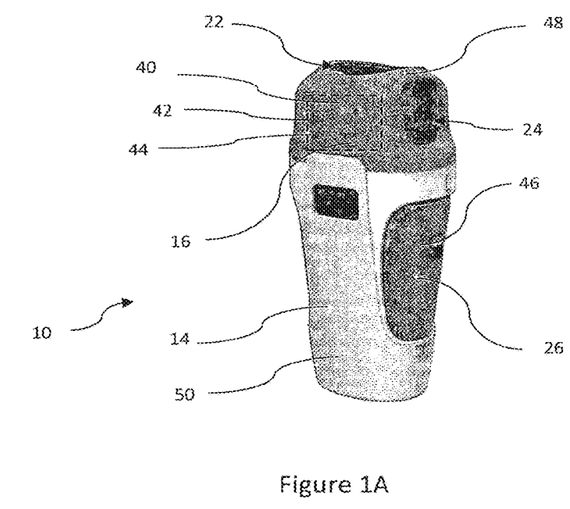
FIGS. 1A and 1B are perspective views of an assistance device according to one embodiment, FIG. 1A representing the assistance device alone and FIG. 1B representing the upper part of the assembly of the assistance device and of a dispensing device connected to the assistance device, the assistance device being in the open position and the dispensing device being provided with a cap for protecting the dispensing orifice.
Figure 1B:
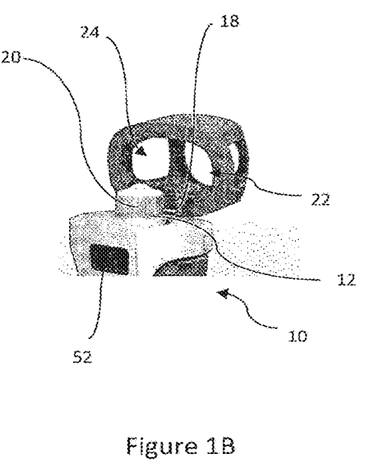

FIG. 1A illustrates an assistance device 10 for assisting in the use of a device 12 for dispensing a liquid product in the form of drops, the liquid product being contained in a tank of the dispensing device 12 (shown on FIG. 1B). FIG. 1B illustrates a dispensing kit comprising the assistance device 10 and the dispensing device 12, which is arranged inside the assistance device 10. The assistance device 10 comprises means for connecting to the dispensing device 12 to form an integral assembly. The connection means may comprise, for example, means for clipping the dispensing device 12 into the assistance device 10. The assistance device 10 comprises a main body 14 in which the dispensing device 12 is placed, and a bearing structure 16 to be pressed against the user's skin when dispensing drops into a target organ of a user (or subject), for example an eye. The bearing structure 16 is, for example, removably mounted on the main body 14 between an open position for inserting the dispensing device 12, shown on FIG. 1B, and a closed use position, for example by means of a hinge 18. The bearing structure 16 can be designed to be flexible enough to rest comfortably against the user's skin and adapt to the different reliefs near the target organ, and/or rigid enough to provide support when pressing and impose a predetermined distance between the target organ and a dispensing orifice 20 (shown on FIGS. 2A and 2B), which is arranged in this example on the dispensing device 12 but which could be arranged according to a variant on the assistance device 10). The bearing structure 16 comprises an axial orifice 22 intended to allow drops of liquid product to fall from the dispensing orifice 20 towards the user's organ. The bearing structure 16 optionally comprises recesses 24 on two opposite sides and at its end, in particular to prevent the user's eye from being in the dark when the assistance device 10 is applied against the user's skin around the eye. The bearing structure 16 may have a contour that is closed or not, for example a C-shaped contour. The C-shaped contour allows, for example, the user to place a finger through the opening of the C to pull the lower eyelid in order to open the eye wider and ensure that the drop reaches the eye.

The assistance device 10 also comprises a bearing area 26 intended in this case to allow the user both to grip and to press in order to dispense the liquid product. The bearing area 26 is arranged on two opposite sides of the main body 14. An activation pressure exerted on the bearing area 26 is transmitted to the tank of the dispensing device 12, in particular at a contact area between the tank and the assistance device 10. The bearing area 26 may be made from a different material, in particular more flexible than that of the rest of the main body 14. It may also comprise reliefs to facilitate gripping by the user. Furthermore, due to the presence of the bearing area 26, the assistance device 10 increases the user's gripping area and the activation pressure area on the tank compared with that of the dispensing device 12 alone, which is particularly advantageous for users with neuromuscular diseases.

Figure 2A:
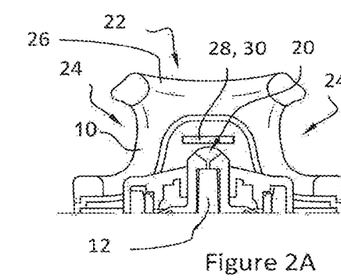
FIGS. 2A and 2B are schematic longitudinal cross-sectional views of different parts of the assembly of FIG. 1B.
Figure 2B:
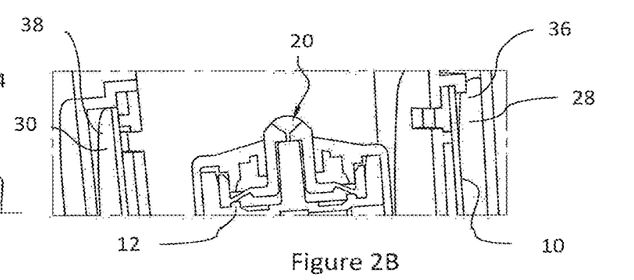
Figure 3:
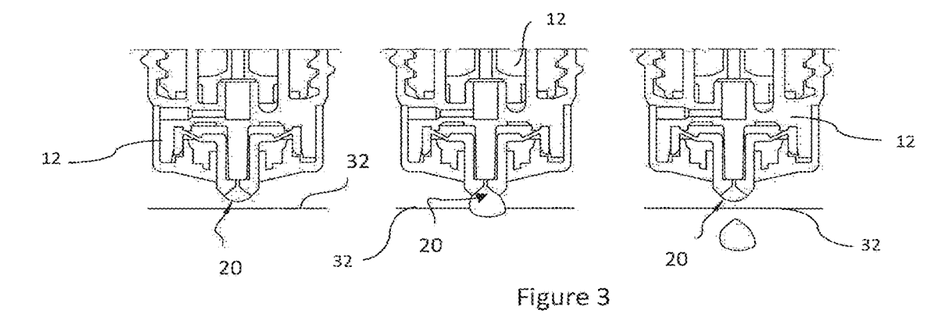
FIG. 3 is a set of three longitudinal cross-sectional views of the upper part of the dispensing device of FIG. 1B.

The assistance device 10 comprises means 28, 30, 36, 38 for detecting liquid product which are arranged near the dispensing orifice 20. FIGS. 2A and 2B show that these detection means comprise first detection means 28, 30 configured such that the detection of the presence of liquid is indicative of a drop in the course of being formed, in contact with the dispensing orifice 20, and comprising optical means consisting of a transmitter 28 and a receiver 30 of an optical detection signal 32 (shown on FIG. 3 and subsequently referred to as optical signal 32) configured to detect the presence of liquid disturbing the optical signal 32 and to measure the duration of this presence. The transmitter 28 comprises, for example, infrared-emitting diodes and the receiver 30 comprises for example phototransistors capable of detecting infrared rays. The transmitter 28 and the receiver 30 detect the presence of a drop passing through the optical signal 32 when the optical signal 32 is disturbed, for example by a variation in the intensity of this optical signal 32. The first detection means 28, 30 are preferably located at a distance of between 1 and 3 mm, preferably 2 mm, from the dispensing orifice 20, detecting the presence of liquid in the detection area located between the transmitter 28 and the receiver 30 near the dispensing orifice 20. The assistance device 10 advantageously comprises second detection means 36, 38, comprising another transmitter 36 and receiver 38 pair located at a distance from the dispensing orifice 20 which is greater than that of the first transmitter 28 and receiver 30 pair. The operation of this second pair 36, 38 is similar to that of the first pair. Preferably, the second detection means 36, 38 are located at a distance of between 5 and 10 mm, for example about 7 mm from the dispensing orifice 20.

Furthermore, with a receiver 30, 38 of limited dimensions, when the assistance device 10 is inclined, the passage of a drop may not be detected by this receiver 30. To overcome this problem, the receiver 30, 38 may have a reception area for receiving the optical signal 32 extending axially and/or circumferentially, the transmitter 28, 36 being configured to transmit said optical signal 32 into the reception area to guarantee that the passage of a drop is detected even when the assistance device 10 is inclined.

The assistance device 10 comprises a system 40 for processing information, in particular detection information provided by the detection means 28, 30, 36, 38. The processing system 40 is configured to provide information on the dispensing of a drop. The information processing system 40 is a system comprising a set of components (mechanical, electronic, chemical, photonic and/or biological) capable of processing information automatically. It comprises, for example, a printed circuit board (PCB), a set of transistors and/or a computer.

The assistance device 10 comprises means 42 for measuring the duration of the presence of a drop near the orifice, for example by measuring the time during which the signal of the detection means is disturbed. The measurement means 42 comprise for example an electronic time counter activated at the same time as the detection means.

The assistance device 10 further comprises means 44 for measuring the inclination, configured to provide information on the inclination of the dispensing device 12 connected to the assistance device 10. In one example, the means 44 for measuring the inclination comprise an inclinometer such as an electronic gyroscope or an accelerometer. The means 44 for measuring the inclination are preferably placed in the main body 14 or in the bearing structure 16, for example in an area intended to be placed near the dispensing orifice 20.

The assistance device 10 further comprises means 46 for measuring the activation pressure exerted on a bearing area to activate the dispensing of a drop, such as the bearing area 26, to trigger the detection means 28, 30, 36, 38 and/or provide information to the processing system 40. The means 46 for measuring the activation pressure may provide information on the magnitude of the activation pressure applied on the bearing area and the time during which this activation pressure is applied. This activation pressure can be detected directly, by measuring the pressure applied by the user on the bearing area 26 to activate the dispensing device 12, or indirectly, for example by measuring the pressure exerted on an area of the assistance device 10 or of the dispensing device 12 connected to the tank of the dispensing device 12 during the activation pressure by the user on the tank or on another bearing area. In this second case, it could be the deformation of the tank which activates the dispensing of a drop, the information of the activation pressure being deduced from the way in which the tank is deformed. The means 46 for measuring the activation pressure comprise, for example, a pressure sensor of the force-sensing resistor (FSR) type, intended to be placed in contact with the tank of the dispensing device 12, being attached for example to the inner side of the assistance device.

The assistance device 10 comprises means 48 for detecting contact with the skin of a user, located on the bearing structure 16. The means 48 for detecting contact can be used to provide information to the processing system 40 on the correct positioning of the target organ opposite the dispensing orifice 20 in order to guarantee that the drop is dispensed at the right place. The means 48 for detecting contact may be optical (light sensor which detects the presence or absence of light at the surface of the bearing structure 16), electrical (closure of an electrical circuit by the presence of the skin), mechanical or based on any other principle.

The assistance device 10 comprises means 50 for measuring the weight of the dispensing device 12 connected to the assistance device 10, configured to provide information on the amount of liquid product remaining in the tank of the dispensing device 12. The means 50 for measuring the weight comprise a weight sensor, for example of the Force Sensing Resistor (FSR) type, which is arranged under or above the tank of the dispensing device 12 to measure the weight of the dispensing device 12 and deduce the weight, and therefore the volume, of the amount of liquid remaining in the tank. In another variant, the assistance device 10 comprises several weight sensors which are arranged around the tank to measure the weight of the dispensing device 12 connected to the assistance device 10, regardless of its inclination.

Advantageously, the assistance device 10 comprises means 52 for indicating the information provided by the processing system 40, for example visual means 52, audible means and/or tactile means. They comprise, for example, a screen to display information alphanumerically. In a variant, they further or alternatively comprise light-emitting diodes around the dispensing orifice 20 in order to provide a light signal to indicate, for example, the correct or incorrect dispensing of a drop of liquid product.

Optionally, the assistance device 10 may further comprise means for blowing a residual drop, such as an air nozzle directed towards the dispensing orifice 20.

We will now describe the method for monitoring the dispensing of a drop using the detection means 28, 30 which are arranged near the drop dispensing orifice 20, and the system 40 for processing the information provided by the detection means 28, 30. This monitoring method is partly illustrated by FIGS. 3 and 4.

Under normal conditions of use of the dispensing device 12, when a user exerts a pressure on the bearing area 26, a drop of liquid product forms at the dispensing orifice 20. The detection means 28, 30 which are arranged near the dispensing orifice 20 detect in a step of detecting the absence of liquid D1, subsequently referred to as the first detection step D1 (shown on FIG. 3A), before the drop formation, an absence of disturbance of a detection signal (by detecting for example an infrared signal of high intensity), indicating an absence of liquid and therefore of a drop in the detection area, and in a step of detecting the presence of liquid D2, subsequently referred to as the second detection step D2 (shown on FIG. 3B), after the start of the drop formation, a disturbance of the detection signal indicating the presence of liquid and therefore of a drop (by detecting a decrease in the intensity of the infrared signal). Once the drop has formed, it detaches from the dispensing orifice 20 and the disturbance of the detection signal disappears during a step of detecting the absence of liquid D3, referred to as the third detection step D3 shown on FIG. 3C (the detection means 28, 30 detect once more an infrared signal of high intensity). The detection means 28, 30 send this series of "absence, presence, absence" information to the processing system 40, which processes it in order to deduce the appearance and the correct dispensing of a drop. If this series of "absence, presence, absence" is not detected, the processing system 40 deduces that there is no correct dispensing of a drop, since no drop has formed and/or the drop has not detached from the dispensing orifice 20.

When the assistance device 10 comprises second detection means 36, 38, during the third detection step D3, an absence of liquid is detected at the first distance from the dispensing orifice 20, using the first detection means 28, 30, and simultaneously or successively, during a step of detecting the presence of liquid subsequently referred to as the fourth detection step, a presence of liquid is detected at the second distance from the dispensing orifice 20, using the second detection means 36, 38. Since the absence of liquid is detected at a distance from the dispensing orifice 20 that is smaller than the distance at which a presence of liquid is detected, the processing system 40 deduces that the drop has detached from the dispensing orifice 20 and has been correctly dispensed.

Figure 4:
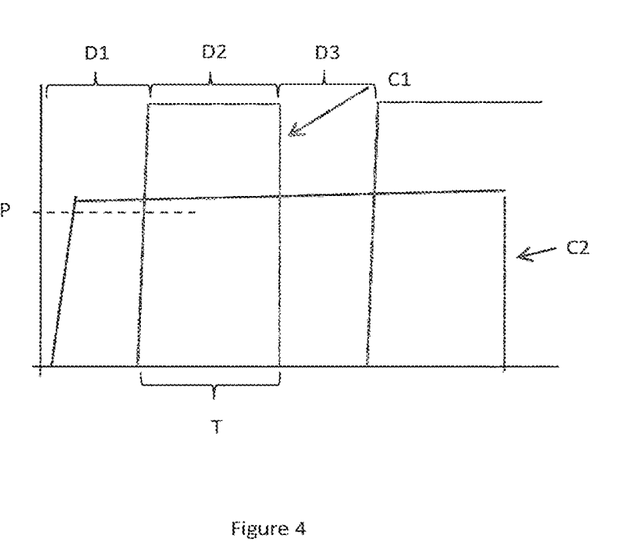
FIG. 4 is a graph showing information processed by the assistance device of FIG. 1A.

On the graph of FIG. 4, the curve C1 shows the disturbance of the detection signal against time and the curve C2 shows the pressure (i.e. the magnitude of the force) exerted on the dispensing device 12 against time.

To obtain the curve C1, in addition to measuring the disturbance by the detection means 28, 30, 36, 38, the duration of presence or absence of signal disturbance, representing the duration corresponding to each detection step, is also measured. In particular, the time elapsed T between the start of the second detection step D2 and the start of the third detection step D3 is measured. The processing system 40 assigns an incorrect dispensing of a drop when the time elapsed is less than a first predetermined duration threshold T1, since the volume of the dispensed drop is considered to be different from a theoretical volume. When the time elapsed T is greater than a second predetermined duration threshold T2, the processing system assigns an incorrect dispensing since it considers that the drop has probably not been dispensed into the target organ, since the drop could have detached when the user was no longer holding the dispensing device 12 opposite the eye. Thus, unless the processing system 40 has received information to the contrary from other measurement or detection means relating to the use of the dispensing device 12, when the elapsed time T is between a first predetermined duration threshold T1 and a second predetermined duration threshold T2 greater than T1, the processing system 40 assigns a correct dispensing. In each of these three cases, the user can be informed by providing corresponding information via the indication means 52.

The time T which corresponds to the duration of formation of the drop of liquid product can be used to estimate the volume of this drop. To do this, a theoretical drop volume is first determined, in this case depending on the geometric characteristics of the dispensing orifice 20 and the viscosity of the liquid product, and preferably also on other characteristics of the dispensing device 12, then the time elapsed T between the start of the second detection step D2 and the start of the third detection step D3 is measured, this time then being used to weight the theoretical drop volume and estimate a volume of the dispensed drop.

The curve C2 is obtained by monitoring the pressure exerted on the bearing area 26 of the dispensing device 12 over time. When the pressure is less than a predetermined pressure threshold P at the start of the third detection step D3, or when the pressure is exerted for a duration less than a predetermined duration, the processing system 40 assigns an incorrect dispensing of a drop.

Also, or as a variant, the pressure exerted on the bearing area 26 to activate the means 28, 30 for detecting liquid product, or other means of the assistance device 10, can be monitored, when the pressure exceeds a predetermined, a priori relatively low pressure threshold so that the detection means 28, 30, 36, 38 can detect the absence of a drop during the first detection step D1, before the start of the second detection step D2. Thus, the detection means 28, 30, 36, 38 or the other means can be put on standby when the assistance device 10 is not being used. According to a variant of the monitoring method, the first detection step D1 can be replaced by a step of detecting activation of a drop dispensing, for example following a pressure exerted on a bearing area 26 or a certain inclination of the dispensing device 12. In this case, the drop may form before activation of the detection means 28, 30 and the first detection step D1 does not occur.

Also or as a variant, the inclination of the dispensing device 12 from the horizontal can be measured. When the inclination variation exceeds a predetermined value during the second detection step D2, indicating that the user is making a sudden movement of the dispensing device 12 connected to the assistance device 10 during the drop formation step, it may assume that the dispensing device 12 is in a position quite different from the liquid product dispensing position, or that the drop has fallen due to shaking, and therefore that the situation is not conducive to correct dispensing. In this case, the processing system 40 assigns an incorrect dispensing of a drop.

The monitoring method also, or as a variant, comprises a step of weighing the dispensing device 12 to deduce the amount of liquid product remaining in the tank. By comparing the weight obtained with the weight of the dispensing device 12 before dispensing any drops, the processing system 40 can detect or validate the dispensing of a drop if there is any weight variation.

Also, or as a variant, a contact between the bearing surface of the bearing structure 16 and the skin of the subject can be detected, for example using an electrical circuit which closes when the skin of the subject connects two electrodes which are arranged on the bearing surface of the bearing structure 16. When the processing system 40 receives positive or negative information regarding the presence of contact, it can assign a correct or incorrect dispensing of a drop, or allow the dispensing of liquid product only if a contact is detected.

The user can be informed when the processing system 40 does not receive the information corresponding to the series of the three steps, or at least of the second detection step D2 and of the third detection step D3, or when the processing system 40 assigns an incorrect dispensing of a drop, for example by a visual, audible or tactile signal.

The amount of dispensed liquid product can also be estimated by estimating the volume of each dispensed drop using the assistance device 10. To do this, a theoretical volume is first determined, for example based on the geometric characteristics of the dispensing orifice 12 and the viscosity of the liquid product, and preferably on other characteristics of the dispensing device 12. The volume of the detected drop is then estimated by weighting this theoretical volume, taking into account at least one of the above-mentioned parameters, i.e.:
- the magnitude of the activation pressure applied by the user on the tank to cause the formation of the drop,
- the variation profile of this activation pressure over time,
- the inclination of the assistance device 10 and of the dispensing device 12,
- the time during which a signal provided by the optical means 28, 30, 36, 38 is disturbed,
- the measurement of the weight of the dispensing device 12.

To weight the theoretical volume, the information system calculates one or more coefficients from one or the combination of the above parameters and applies it by multiplication to the calculated theoretical volume.

Figure 5:
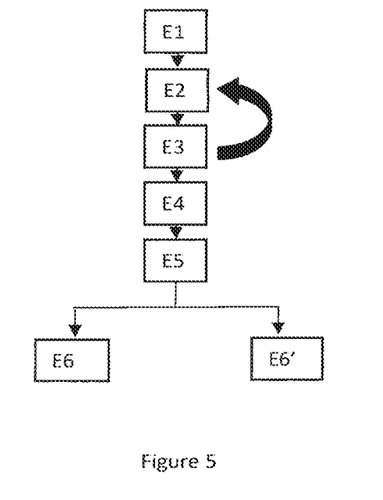
FIG. 5 is a graph showing the steps of a monitoring method according to one embodiment.

FIG. 5 describes an example of the steps of a monitoring method. The monitoring method starts with a first step E1 of detecting an activation pressure exerted by the user on the bearing area 26. When the detected activation pressure exceeds a predetermined threshold, for example 15 N, the detection means 28, 30 are then activated to detect a drop in a step E2. Other means of the assistance device 10 can also be activated at this time. The detection means 28, 30 monitor the area where the drop is formed near the dispensing orifice 20 until they detect the presence of a liquid in step E3, corresponding to the second detection step D2. A time counter is started at step E4 when the liquid is detected. The time is counted until the drop leaves the formation area monitored by the detection means 28, 30, i.e. until the drop detaches from the dispensing orifice 20. In a step E5, the detection means 28, 30, 36, 38 detect the absence of liquid during the third detection step D3, and a pressure test is performed. If, during this test, the pressure exerted on the bearing area 26 does not reach a predetermined pressure threshold, for example 15 N, then it is considered that the drop has not detached under the effect of an optimum exerted pressure, and the processing system 40 assigns an incorrect dispensing. If, during the test, the pressure exceeds the predetermined threshold, then the processing system assigns a correct dispensing (in step E6' unless the processing system 40 has received information to the contrary from other measurement or detection means relating to the use of the dispensing device 12). In addition, the processing system 40 may process information on the inclination of the dispensing device 12 connected to the assistance device 10 and/or information provided by the detection means 28, 30. For example, if the optical signal is no longer disturbed but the processing system 40 receives information indicating a significant change in inclination, this means that the drop of liquid product has been dispensed at the wrong location, for example has fallen beside the dispensing orifice 20. Advantageously, if the processing system 40 still detects a disturbance of the optical signal 32 in step E4 after a predetermined duration threshold, step E5 is started and if the pressure measured is less than the predetermined pressure threshold, this means that there is a residual drop at the dispensing orifice 20, this being confirmed by the fact that the second detection step D2 is still in progress.

According to another embodiment, not illustrated, the pressure test is performed during the second detection step. If, during this test, the pressure exerted on the bearing area 26 does not exceed the predetermined pressure threshold for a predetermined duration, then it is considered that the drop has not detached under the effect of an optimum exerted pressure, and the processing system 40 assigns an incorrect dispensing.

The invention is not limited to the embodiments described and other embodiments will be clearly apparent to those skilled in the art.

The invention claimed is:

1. A method for monitoring a dispensing of a drop by a device for dispensing a liquid in a form of drops, using a detector for detecting the liquid, said detector is arranged near an orifice for dispensing the drops of the liquid, and a system for processing information provided by the detector, a monitoring method during which the processing system receives information corresponding to the following series of steps:
   - a step of detecting a presence of the liquid, during which the detector detects the presence of the liquid near the dispensing orifice, the detector being configured such that the detection of the presence of the liquid is indicative of the drop of the liquid while being formed, the drop being in contact with the dispensing orifice,
   - after the step of detecting the presence of the liquid, a step of detecting an absence of the liquid, during which the detector detects the absence of the liquid near the dispensing orifice
   - and the processing system processes information on the series of steps of detecting the presence of the liquid and detecting the absence of the liquid in order to provide information on the dispensing of the drop, wherein the processing system identifies an occurrence of a sequence of the step of detecting the presence of the liquid followed by the step of detecting the absence of the liquid to indicate the dispensing of the drop, wherein the step of detecting the absence of the liquid of the sequence is a last step of liquid detection steps of the sequence.

2. The monitoring method according to claim 1, wherein the step of detecting the absence of the liquid is referred to as a third detection step and further comprising, before the step of detecting the presence of the liquid, referred to as a second detection step, a first step of detecting an absence of the liquid, referred to as a first detection step, during which the detector detects the absence of the liquid near the dispensing orifice wherein the sequence comprises, in order, the first detection step followed by the second detection step and followed by the third detection step.

3. The monitoring method according to claim 1, comprising, before the step of detecting the presence of the liquid, referred to as a second detection step, a step of detecting activation of the dispensing of the drop.

4. The monitoring method according to claim 1, wherein the detector transmits a detection signal near the dispensing orifice, receives said transmitted detection signal and detects the presence of the liquid by receiving the detection signal that is disturbed compared with the detection signal received in the absence of the liquid.

5. The monitoring method according to claim 4, comprising:
a step of determining the theoretical drop volume,
a step of estimating the volume of the dispensed drop comprising a step of weighting the theoretical drop volume, during which at least one of the following parameters is taken into account to perform this weighting:
a magnitude of the activation pressure applied by the user on a tank to cause formation of the drop,
a variation profile of this activation pressure over time,
inclination of the dispensing device,
a time during which a signal provided by the detector is disturbed, and
measurement of the weight of the dispensing device.

6. The monitoring method according to claim 1, during which a time elapsed between a start of the step of detecting the presence of the liquid and the start of the step of detecting the absence of the liquid is measured and the processing system assigns an incorrect dispensing of the drop when the time elapsed is less than a first predetermined duration threshold.

7. The monitoring method according to claim 1, during which a time elapsed between a start of the step of detecting the presence of the liquid and the start of the step of detecting the absence of the liquid is measured and the processing system assigns an incorrect dispensing of the drop when the time elapsed is greater than a second predetermined duration threshold.

8. The monitoring method according to claim 1, comprising steps of:
determining a theoretical drop volume,
measuring a time elapsed between the start of the step of detecting the presence of the liquid and the start of the step of detecting the absence of the liquid, and
using this elapsed time to weight the theoretical drop volume and estimate a volume of the dispensed drop.

9. The monitoring method according to claim 1, during which a pressure exerted on a bearing area to activate dispensing of the drop is monitored and the detector is activated when the pressure exceeds a predetermined pressure threshold.

10. The monitoring method according to claim 1, during which displacement of a bearing area, is monitored, and the processing system assigns an incorrect dispensing of the drop when a time elapsed is less than a first predetermined duration threshold.

11. The monitoring method according to claim 1, during which inclination of the dispensing device is measured and the processing system uses this measurement to estimate the volume of the drop detected.

12. The monitoring method according to claim 1, during which a contact between a bearing surface of an assistance device for assisting in the use of the dispensing device and a skin of a subject is detected and during which the processing system processes this information to assign a correct dispensing of the drop.

13. The monitoring method according to claim 1, during which a user is informed when the processing system does not receive the information corresponding to the series of the two steps of detecting the presence of the liquid and the absence of the liquid, or even when the processing system does not receive the information corresponding to the series of the three steps of detecting the absence of the liquid, the presence of the liquid and the absence of the liquid, or even when the processing system assigns an incorrect dispensing of the drop.

14. The monitoring method according to claim 1, during which weight of the dispensing device is measured to deduce the amount of the liquid remaining in the dispensing device.

15. An assistance device for assisting in the use of a device for dispensing the liquid in the form of drops for implementing the monitoring method according to claim 1, comprising the detector for detecting the liquid, the processing system and at least one element from a group consisting of:
a measuring device for measuring inclination,
a detector for detecting pressure on a bearing area,
a detector for detecting contact with a skin of a user, and
a measuring device for measuring weight.

16. The assistance device according to claim 15, comprising a measuring device for measuring a time elapsed between the start of the step of detecting the presence of the liquid and a start of the step of detecting the absence of the liquid.

17. The assistance device for assisting in the use of a device for dispensing the liquid in the form of drops for implementing the monitoring method according to claim 1, comprising the detector for detecting the liquid, the detector for detecting the liquid comprising a first detector configured to detect the liquid at a first distance from the dispensing orifice, such that the detection of the presence of the liquid is indicative of the drop while being formed, in contact with the dispensing orifice, and a second detector configured to detect the liquid at a second distance from the dispensing orifice, the second distance being greater than the first distance.

18. The monitoring method according to claim 1 wherein the processing system processes the detection of the presence of the liquid followed by the detection of the absence of the liquid in order to identify the drop having been dispensed to provide the information on the dispensing of the drop.

19. A method for monitoring a dispensing of a drop by a device for dispensing a liquid in a form of drops, using a detector for detecting the liquid, said detector is arranged near an orifice for dispensing the drops of the liquid, and a system for processing information provided by the detector, a monitoring method during which the processing system receives information corresponding to the following series of steps:
a step of detecting a presence of the liquid, during which the detector detects the presence of the liquid near the dispensing orifice, the detector being configured such that the detection of the presence of the liquid is indicative of the drop of the liquid while being formed, the drop being in contact with the dispensing orifice,
after the step of detecting the presence of the liquid, a step of detecting an absence of the liquid, during which the detector detects the absence of the liquid near the dispensing orifice and the processing system processes information on the series of steps of detecting the presence of the liquid and detecting the absence of the liquid in order to provide information on the dispensing of the drop; wherein a pressure exerted on a bearing area to activate the dispensing of the drop is monitored and the processing system assigns an incorrect dispensing of the drop when the pressure is less than a predetermined pressure threshold.

20. A method for monitoring a dispensing of a drop by a device for dispensing a liquid in a form of drops, using a detector for detecting the liquid, said detector is arranged near an orifice for dispensing the drops of the liquid, and a system for processing information provided by the detector, a monitoring method during which the processing system receives information corresponding to the following series of steps:
- a step of detecting a presence of the liquid, during which the detector detects the presence of the liquid near the dispensing orifice, the detector being configured such that the detection of the presence of the liquid is indicative of the drop of the liquid while being formed, the drop being in contact with the dispensing orifice,
- after the step of detecting the presence of the liquid, a step of detecting an absence of the liquid, during which the detector detects the absence of the liquid near the dispensing orifice and the processing system processes information on the series of steps of detecting the presence of the liquid and detecting the absence of the liquid in order to provide information on the dispensing of the drop;
- wherein inclination of the dispensing device is measured, and the processing system assigns an incorrect dispensing of the drop when the inclination variation exceeds a predetermined value during the step of detecting the presence of the liquid.

* * * * *